United States Patent
Muramatsu et al.

[11] Patent Number: 6,111,342
[45] Date of Patent: Aug. 29, 2000

[54] INSTRUMENT FOR CHEMICAL MEASUREMENT

[75] Inventors: Hiroshi Muramatsu; Tatsuaki Ataka, both of Tokyo, Japan

[73] Assignee: Seiko Instruments Inc., Japan

[21] Appl. No.: 08/209,638

[22] Filed: Mar. 10, 1994

[30] Foreign Application Priority Data

Mar. 19, 1993 [JP] Japan ..................................... 5-57554

[51] Int. Cl.[7] ................................................ H01L 41/08
[52] U.S. Cl. ........................ 310/366; 310/311; 310/363; 310/316.01; 310/317
[58] Field of Search ..................................... 310/311, 312, 310/363–365, 321–324, 328, 334, 330–332, 316, 317, 319; 340/603, 604, 620; 204/280, 400, 403, 404, 411, 412, 434; 435/4, 817; 436/149, 806; 422/56, 57, 68.1, 88, 98, 82.01, 82.02; 73/19, 23, 24, 24.03, 28–30, 61 R, 61.1 R, 61.2, 61.45, 61.49

[56] References Cited

U.S. PATENT DOCUMENTS

| | | | |
|---|---|---|---|
| 3,253,219 | 5/1966 | Littler | 310/363 X |
| 3,561,253 | 2/1971 | Dorman | 310/312 X |
| 3,879,992 | 4/1975 | Bartera | 73/30 |
| 4,325,060 | 4/1982 | Purtell et al. | 340/604 |
| 4,469,976 | 9/1984 | Scott | 310/366 X |
| 4,561,286 | 12/1985 | Sekler | 73/23 |
| 4,789,804 | 12/1988 | Karube et al. | 310/311 |
| 5,132,643 | 7/1992 | Ueno et al. | 310/366 X |
| 5,283,037 | 2/1994 | Baer et al. | 422/82.01 |
| 5,306,644 | 4/1994 | Myerholtz et al. | 436/149 |
| 5,334,303 | 8/1994 | Muramatsu et al. | 204/412 |

*Primary Examiner*—Mark O. Budd
*Attorney, Agent, or Firm*—Adams & Wilks

[57] ABSTRACT

A quartz oscillator for detecting a physicochemical change in a substance to be measured comprises a first electrode having at least two separate electrode portions for contact with the substance to be measured, and a second electrode. A chemical measuring instrument comprises a piezoelectric characteristic-measuring circuit having an output signal line connected to capacitors connected in parallel to the separate electrode portions of the first electrode of the quartz oscillator. An input signal line of the piezoelectric characteristic-measuring circuit is connected to the second electrode of the quartz oscillator. A voltage application circuit is connected to one of the separate electrode portions of the first electrode for applying a voltage between the separate electrode portions. An electrical current-measuring circuit is connected to the other of the separate electrode portions which is electrically grounded. The resonant characteristics of the quartz oscillator and the conductivity on the surfaces of the electrodes can be simultaneously and effectively measured.

16 Claims, 3 Drawing Sheets

FIG. 1A    FIG. 1B
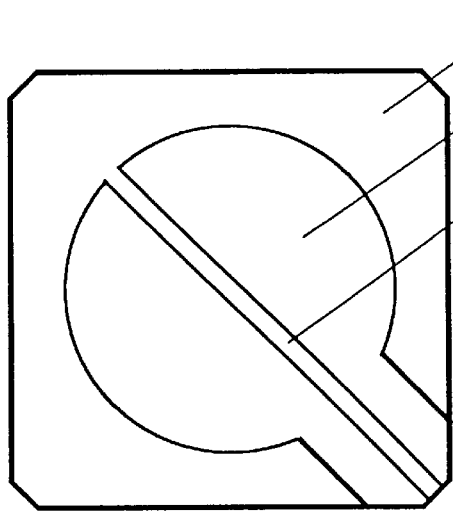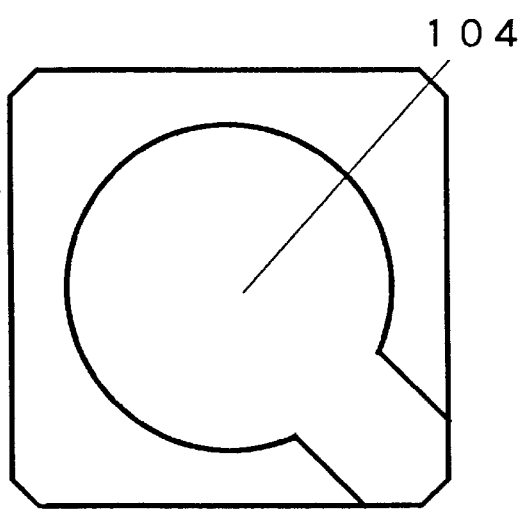
FIG. 2A    FIG. 2B
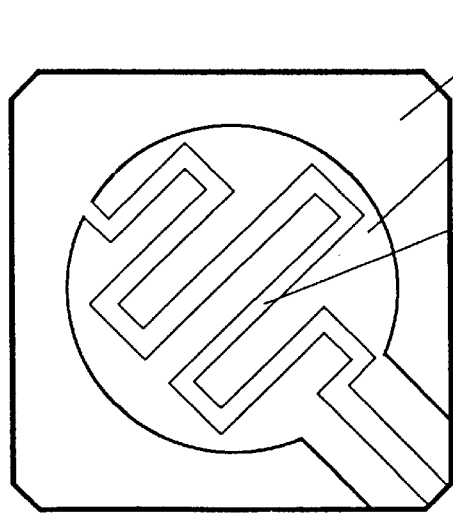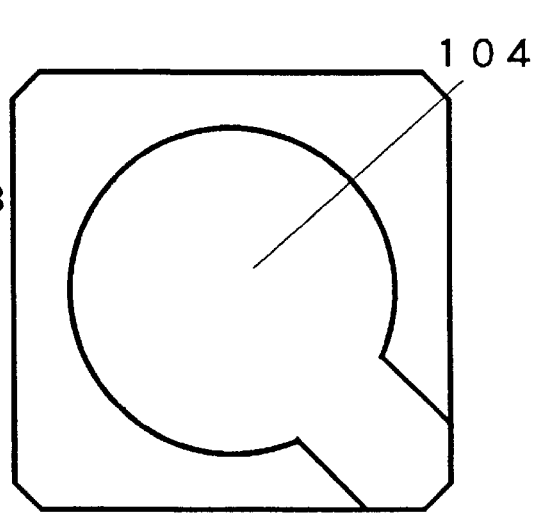

INSTRUMENT FOR CHEMICAL MEASUREMENT

BACKGROUND OF THE INVENTION

The present invention relates to a quartz oscillator and a chemical measuring instrument used for measurements in chemical, physicochemical, biochemical, food, medical, and chemical industry applications.

A known chemical measuring instrument using a quartz oscillator measures a change in the resonant frequency of the quartz oscillator and a change in the resonant resistance simultaneously. This instrument is effective in measuring adsorption and release of a substance to be investigated onto and from the surface of the quartz oscillator, as well as a change in the viscoelasticity. Where the instrument is combined with an electrochemical measuring instrument, changes in current and voltage caused by an electrochemical reaction can be simultaneously measured. On the other hand, an electrochemical measuring procedure using comb-shaped electrodes is effective in measuring the characteristics of the conductivity of a thin film and quantitating electrochemically active species at low concentrations.

Generally, various measuring methods are used for substances to be investigated. Various results are obtained by the various measuring methods. Since these methods are carried out separately, it is not easy to consider the relations among the results. Furthermore, measurements are required to be conducted repeatedly, thus deteriorating the efficiency.

One electrochemical measuring method using a quartz oscillator and comb-shaped electrodes is characterized in that the method is utilized to measure electrodes coated with a thin film. Another electrochemical measuring method using a quartz oscillator and comb-shaped electrodes is characterized in that they are employed as detecting elements in a liquid chromatograph.

SUMMARY OF THE INVENTION

It is an object of the present invention to provide a highly functional detector which makes use of various measuring methods simultaneously to obtain plural kinds of information in one measurement.

To solve the problems described above, the present invention provides a quartz oscillator for use as a detecting device, the oscillator being characterized in that a first electrode disposed on a first surface of the quartz oscillator and in contact with a substance to be investigated is split into two or more portions and assumes a comb-shaped form. The comb-shaped electrode portions are alternately arranged. The invention also offers a measuring instrument for measuring only conductivity. An output signal line is connected with capacitors which are connected in parallel with the split electrode portions. An input signal line is connected with a second electrode disposed on a second surface of the quartz oscillator. The instrument further of a comprises piezoelectric characteristic-measuring means for measuring the resonant characteristics of the quartz oscillator, voltage application means for applying a voltage between the two split electrode portions, and electrical current-measuring means for measuring an electrical current flowing between the electrode portions. The instrument is used for measuring, for example, a physicochemical change in a substance to be investigated.

The invention also provides an instrument used for electrochemical measurements. An output signal line is connected with capacitors which are connected in parallel with split electrode portions. An input signal line is connected with a counter electrode. The instrument further comprises piezoelectric characteristic-measuring means for measuring the resonant characteristics of the quartz oscillator, a solution with which the split electrode portions are in contact, first voltage application means, electrical current-and-voltage measuring means, second voltage application means for applying a certain voltage to the second one of the split electrode portions relative to the first one of the split electrode portions, and electrical current-measuring means for measuring the electrical current flowing through the second electrode portion. The first voltage application means applies a voltage to the counter electrode so that the split electrode portions may act as working electrodes of an electrochemical measuring circuit, whereby the potential at the working electrodes relative to a reference electrode is controlled. The electrical current-and-voltage measuring means measures an electrical current flowing through the working electrodes when a first one of the split electrode portions is grounded. The instrument is used to measure, for example, a physicochemical change in the substance to be measured.

Measurement of the resonant characteristics of the quartz oscillator having the split electrode portions is enabled by connecting the output signal line of the piezoelectric characteristic-measuring means with capacitors which are connected in parallel with the split electrode portions, and connecting the input signal line of the piezoelectric characteristic-measuring means with the backside electrode. The use of the capacitors has the advantage that an RF signal component from the piezoelectric characteristic-measuring means is separated from the conductivity and that a DC component signal is separated in an electrochemical measurement.

The characteristics of a quartz oscillator contain both variations in the resonant frequency and variations in the resonant resistance. It is possible to know chiefly, from the variations in the resonant frequency, changes in the weight due to adsorption and release of a substance onto and from the surface of the quartz oscillator or a coating film. Also, it is possible to determine, from the variations in the resonant resistance, changes in the viscosity of the liquid crystal in contact with the surface of the quartz oscillator or changes in the viscosity or viscoelasticity of the coating film. At the same time, an electrical current-potential curve can be obtained by combining a conductivity-measuring or electrochemical-measuring system using comb-shaped electrodes with the above-described system.

BRIEF DESCRIPTION OF THE DRAWINGS

FIGS. 1A and 1B are schematic diagram of a first embodiment of a quartz oscillator according to the present invention used for chemical measurements;

FIGS. 2A and 2B are schematic diagrams of a second embodiment of a quartz oscillator according to the present invention used for chemical measurements;

DETAILED DESCRIPTION OF THE PREFERRED EMBODIMENTS

Figure 3:
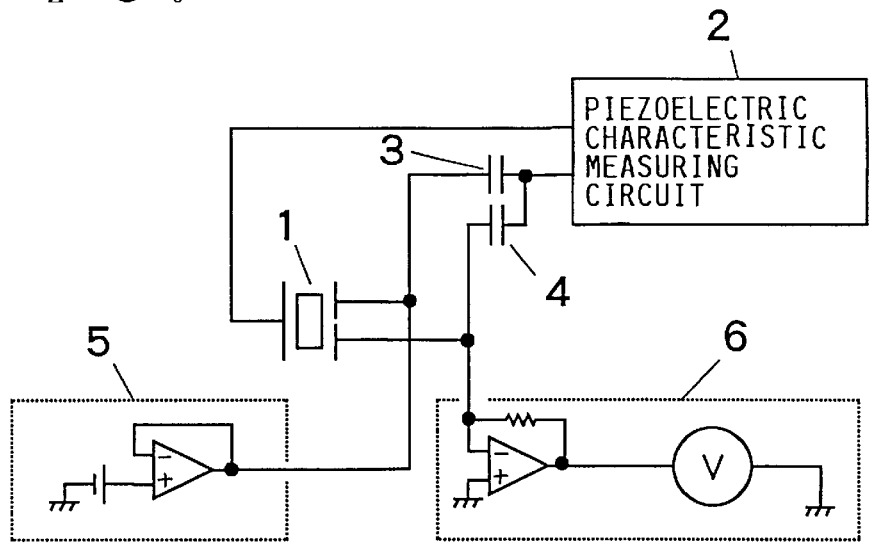
FIG. 3 is a schematic diagram of an instrument for chemical measurements employing a quartz oscillator according to the present invention.

Embodiments of the invention are hereinafter described by referring to the drawings.

(Configuration of Quartz Oscillator for Chemical Measurements)

FIGS. 1A and 1B are schematic diagrams of a quartz oscillator comprising a quartz crystal substrate 101 having a first electrode 102 on a first surface or front side. The first electrode 102 is divided or split into two electrode portions. The oscillator has a second electrode 104 on a second surface or rear side. A quartz oscillator chiefly used in the illustrated embodiment has a fundamental frequency of 9 MHz, measures 8 mm by 8 mm, and has a thickness of about 0.18 mm. The electrodes are formed by depositing gold onto a base layer of chromium by vacuum evaporation. The first electrode 102 on the front side is placed in contact with a substance to be investigated and is divided into two electrode portions by etching a central portion 103 by photolithography techniques. The electrode has a portion extending from the quartz oscillator plate, the portion being electrically connected with a measuring instrument.

FIGS. 2A and 2B are schematic diagrams of a second embodiment of a quartz oscillator comprising a quartz crystal substrate 101 having a first split electrode 105 on its front side having comb-shaped electrode portions which are alternately. The oscillator has a second electrode 104 on its rear side. In a standard experiment, the width of the comb-shaped electrodes and their spacing were set to 15 $\mu$m. In practice, these dimensions can be reduced to approximately 2 $\mu$m.

The electrode on the front side can be further split, and a reference electrode for electrochemical measurements can be formed on the quartz oscillator.

(Instrument for Simultaneous Measurement of Conductivity)

FIG. 3 is a schematic diagram of an instrument used for measurement of conductivity. In FIG. 3, a piezoelectric characteristic-measuring circuit 2 has an output signal line connected with capacitors 3 and 4 which are connected in parallel with the split electrode portions of the first electrode on the front side of a quartz oscillator 1 constructed according to one of the embodiments shown in FIG. 1A or FIG. 2A. The circuit 2 has an input signal line which is connected with a counter electrode or second electrode on the rear side of the quartz oscillator. The circuit 2 can measure the resonant characteristics of a quartz oscillator. At the same time, a voltage application circuit 5 is connected with one of the two split electrode portions of the first electrode. An electrical current-measuring circuit 6 is connected with the other of the split electrode portions which is electrically grounded. The conductivity on the surfaces of the electrodes can be measured by measuring this current.

(Instrument for Simultaneous Measurement of Electrochemical Characteristics)

Figure 4:
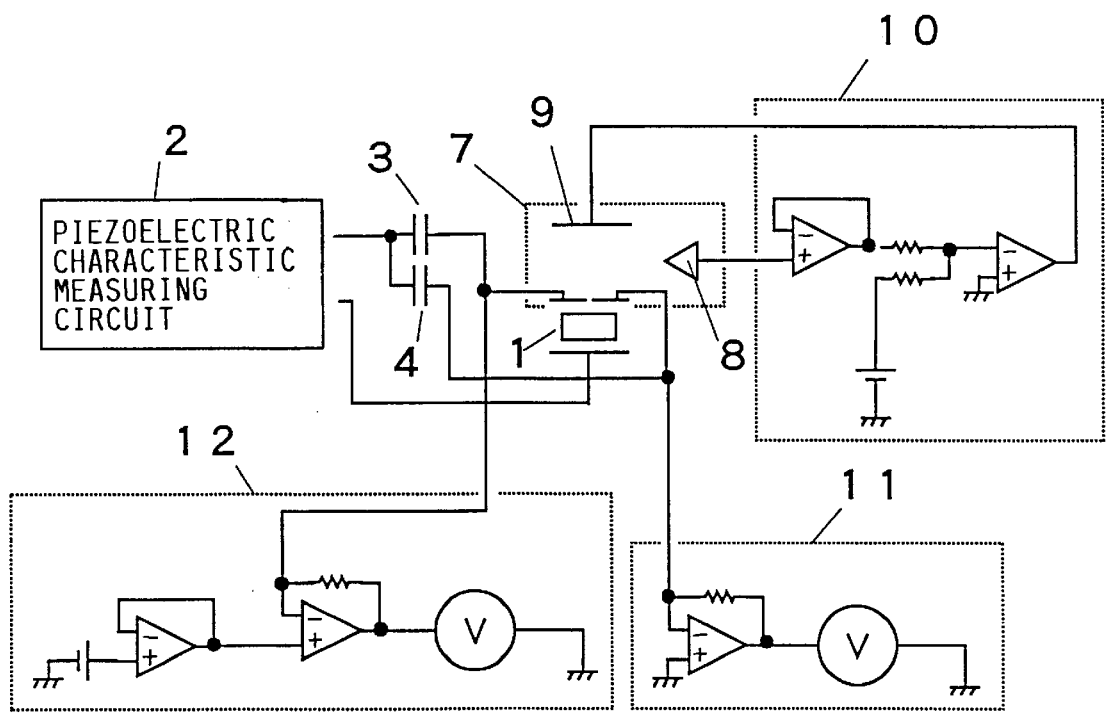
FIG. 4 is a schematic diagram of an instrument for chemical measurements employing an oscillator according to the present invention.

FIG. 4 is a schematic diagram of an instrument for measuring electrochemical characteristics. In FIG. 4, a piezoelectric characteristic-measuring circuit 2 has an output signal line connected with capacitors 3 and 4 which are connected in parallel with the split electrodes of the first electrode on the front side of a quartz oscillator 1 constructed according to one of the embodiments shown in FIG. 1A or FIG. 2A. The circuit 2 has an input signal line which is connected with a counter electrode, or the second electrode on the rear side of the quartz oscillator. Thus, the circuit can measure the resonant characteristics of the quartz oscillator 1. The electrode of the quartz oscillator 1, in this embodiment the first electrode, which is in contact with a substance to be investigated acts as a working electrode and is accommodated in a holder of an electrolytic cell 7 containing an electrolytic solution such that only the electrode is immersed within the electrolytic solution used for measurement of electrochemical characteristics. A reference electrode 8 and another counter electrode, indicated by 9, are held together with the working electrode. A potentiostat circuit 10 for applying a voltage to the counter electrode 9 is connected with each electrode so that an arbitrary potential can be placed on the working electrode relative to the potential on the reference electrode 8. One of the electrode portions of the quartz oscillator is electrically grounded, acts as a first working electrode portion, and is connected with a circuit 11 which measures an electrical current flowing through the working electrode. A circuit 12 is connected to the other of the electrode portions, which acts as a second working electrode portion, and sets an arbitrary potential and measures an electrical current flowing through the second working electrode portion.

(Circuit for Measuring Characteristics of Quartz Oscillator)

Figure 5:
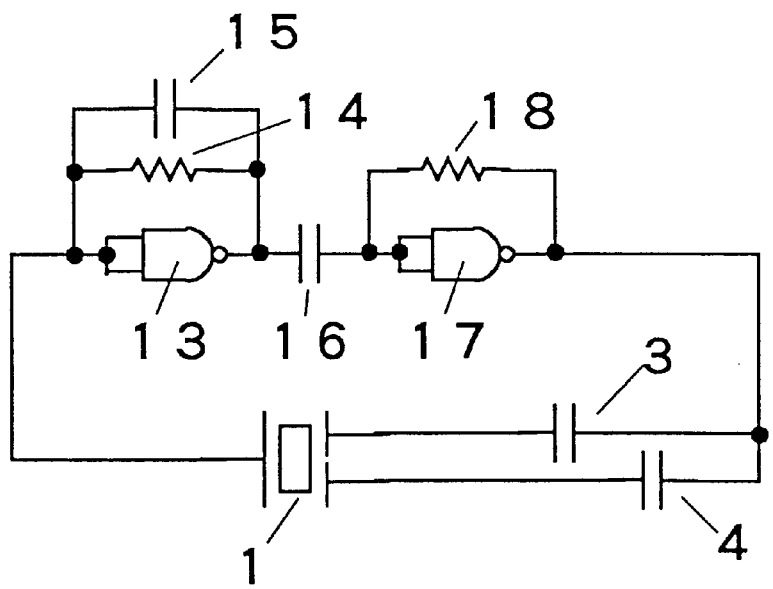
FIG. 5 is a schematic diagram of an oscillator circuit which can be used in the present invention.
Figure 6:
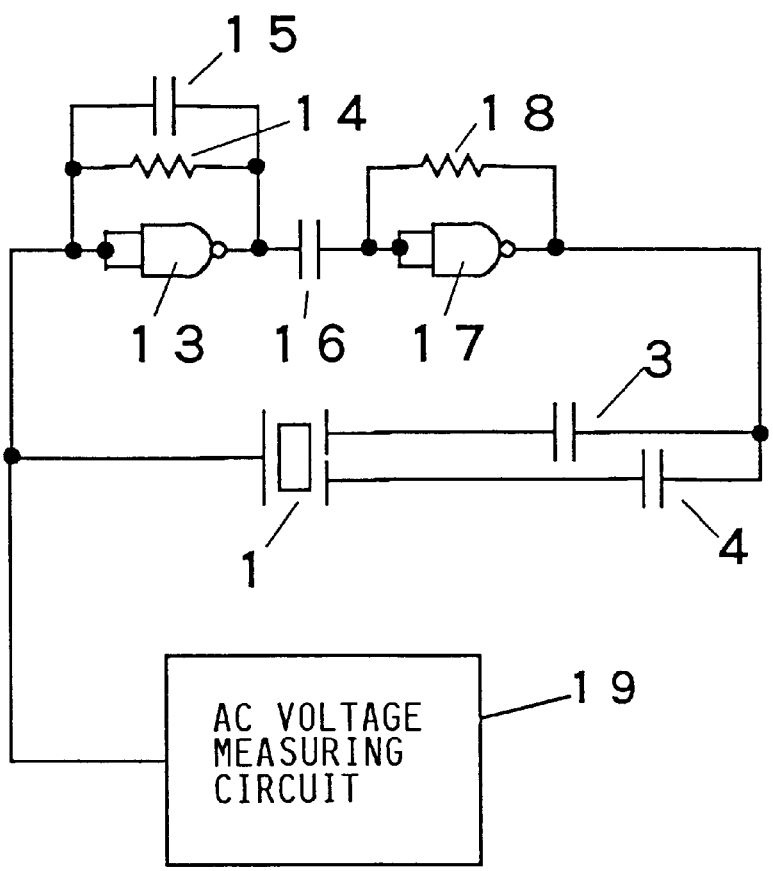
FIG. 6 is a schematic diagram of an oscillator circuit which can be used in the present invention.

An oscillator circuit or an impedance-measuring instrument can be used as the piezoelectric characteristic-measuring circuit 2. A commercially available impedance-measuring instrument can be connected as it is. An example in which an oscillator circuit is used is shown in FIG. 5. In FIG. 5, the electrode of the quartz oscillator which is not in contact with the substance to be investigated is connected with the input of a NAND 13. The input terminal of the NAND is short-circuited. A resistor 14 and a capacitor 15 are connected in parallel with the NAND. The output of the NAND 13 is connected with one terminal of a capacitor 16. The other terminal of the capacitor 16 is connected with the input side of a NAND 17 whose input terminal is short-circuited. A resistor 18 is connected in parallel with the NAND 17. The output side of the NAND 17 is connected with two capacitors 3 and 4 which are connected in parallel with the split electrode portions, respectively, of the quartz oscillator. The circuit shown in FIG. 6 using this oscillator circuit has an AC voltage-measuring circuit 19 for measuring the amplitude of the signal applied to the input of an oscillator circuit, in addition to the circuit of FIG. 5. Thus, the resonant resistance can be measured together with a change in the resonant frequency, for the following reason. The amplitude of the signal applied to the quartz oscillator is constant. The amplitude at the input point of the oscillator circuit varies, depending on the ratio between the impedance of the quartz oscillator and the input impedance of the oscillator circuit.

(Application to Gas Sensor)

Based on the measuring instrument shown in FIG. 3, a sebaceous film was coated on the quartz oscillator to construct a gas sensor. The resonant frequency was varied by a volatile organic gas such as ethanol. Also, the resonant frequency was varied by changes in moisture. Measurement of the conductivity reveals that the resonant frequency was affected minimally by the organic gas but varied according to changes in the moisture. This demonstrates that the resulting measuring instrument is a sensor which can measure changes in an organic gas and changes in moisture simultaneously and separately.

(Application to Liquid Chromatograph Detector)

Based on the measuring instrument shown in FIG. 3, the quartz oscillator was installed in a flow cell such that the split electrodes of the quartz oscillator were in contact with a liquid to be investigated. A change in the viscosity of the sample solution was measured by measuring a change in the resonant frequency or a change in the resonant resistance of the quartz oscillator. At the same time, the conductivity of the liquid was measured from the electrical current flowing between comb-shaped electrodes.

(Application to Electrochemical Measurements)

Based on the measuring instrument shown in FIG. 4, polypyrol was electrolytically deposited as a film on the split electrode portions of the quartz oscillator in a perchloric sodium aqueous solution of pyrol. Using the quartz oscillator sufficiently coated with the polypyrol film, the potential was swept electrochemically within the electrolytic solution. Variations in the resonant frequency caused by movement of ions into the polypyrol film, variations in the resonant resistance reflecting changes in the viscoelasticity induced by oxidation and reduction of the film, and variations in the conductivity caused by the oxidation, reduction of the film and by ion doping could be measured, along with an electrical current-potential curve. It is obvious that this method can be applied to electrodes coated with various high polymers such as polyaniline. It has been proved that this instrument can be effectively used for electrochemical researches.

AT-cut and BT-cut quartz oscillators having fundamental frequencies of 1 to 40 MHz can be used for the instruments described thus far.

A novel sensor system capable of measuring plural items can be fabricated from the inventive quartz oscillator and the inventive instrument for chemical measurements. Also, a new method of conducting electrochemical researches is offered.

What is claimed is:

1. A chemical measuring instrument for detecting a physicochemical change in a substance, the chemical measuring instrument comprising:

a quartz oscillator having a first electrode comprising at least two separate electrode portions and a second electrode;

piezoelectric characteristic measuring means having an output signal line connected to capacitors connected in parallel to the separate electrode portions of the first electrode, and an input signal line connected to the second electrode;

voltage application means for applying a voltage between the separate electrode portions; and electrical current measuring means for measuring an electrical current flowing between the separate electrode portions.

2. A chemical measuring instrument for detecting a physicochemical change in a substance, the chemical measuring instrument comprising:

a quartz oscillator having a first electrode comprising at least two separate electrode portions and a second electrode;

piezoelectric characteristic measuring means having an output signal line connected to capacitors connected in parallel to the separate electrode portions of the first electrode, and an input signal line connected to the second electrode;

an electrolytic cell having a counter electrode and containing an electrolytic solution, the separate electrode portions being immersed in the electrolytic solution;

first voltage application means for applying a voltage to the counter electrode of the electrolytic cell to control an electrical potential of the separate electrode portions which act as a working electrode of the electrolytic cell;

first electrical current measuring means for measuring an electrical current flowing between two of the separate electrode portions when one of the two separate electrode portions is grounded;

second voltage application means for applying a predetermined level of voltage to the other of the two separate electrode portions; and second electrical current measuring means for measuring an electrical current flowing through the other of the electrode portions.

3. A chemical measuring instrument as claimed in claim 1; wherein each of the separate electrode portions comprises a plurality of comb-shaped elements.

4. A chemical measuring instrument as claimed in claim 3; wherein the comb-shaped elements of each of the separate electrode portions are alternately arranged on the quartz oscillator.

5. A chemical measuring instrument as claimed in claim 1; wherein the quartz oscillator further comprises a quartz crystal substrate having first and second surfaces, the first and second electrodes being disposed on the first and second surfaces, respectively, of the quartz oscillator.

6. A chemical measuring instrument as claimed in claim 5; wherein the first and second surfaces of the quartz crystal substrate are substantially opposite one another.

7. A chemical measuring instrument as claimed in claim 5; wherein each of the separate electrode portions comprises a plurality of comb-shaped elements.

8. A chemical measuring instrument as claimed in claim 7; wherein the comb-shaped elements of each of the separate electrode portions are alternately arranged on the first surface of the quartz crystal substrate.

9. A chemical measuring instrument as claimed in claim 2; wherein each of the separate electrode portions comprises a plurality of comb-shaped elements.

10. A chemical measuring instrument as claimed in claim 9; wherein the comb-shaped elements of each of the separate electrode portions are alternately arranged on the quartz oscillator.

11. A chemical measuring instrument as claimed in claim 2; wherein the quartz oscillator further comprises a quartz crystal substrate having first and second surfaces, the first and second electrodes being disposed on the first and second surfaces, respectively, of the quartz oscillator.

12. A chemical measuring instrument as claimed in claim 11; wherein the first and second surfaces of the quartz crystal substrate are substantially opposite one another.

13. A chemical measuring instrument as claimed in claim 11; wherein each of the separate electrode portions comprises a plurality of comb-shaped elements.

14. A chemical measuring instrument as claimed in claim 13; wherein the comb-shaped elements of each of the separate electrode portions are alternately arranged on the first surface of the quartz crystal substrate.

15. A quartz oscillator for detecting a physicochemical change in a substance, the quartz oscillator comprising: a quartz crystal substrate having first and second surfaces; a first electrode disposed on the first surface of the quartz crystal substrate and having at least two separate electrode portions for contact with a substance to detect a physicochemical change in the substance, each of the separate electrode portions comprising a plurality of comb-shaped elements; and a second electrode disposed on the second surface of the quartz crystal substrate.

16. A chemical measuring instrument as claimed in claim 15; wherein the comb-shaped elements of each of the separate electrode portions are alternately arranged on the first surface of the quartz crystal substrate.

* * * * *